United States Patent [19]

Tuttle et al.

[11] Patent Number: 4,946,848
[45] Date of Patent: Aug. 7, 1990

[54] METHOD OF TREATING PRURITUS WITH NALMEFENE AND CLONIDINE

[75] Inventors: Ronald R. Tuttle, Escondido, Calif.; J. R. Thornton, Leeds, England

[73] Assignee: Baker Cumins Dermatologicals, Inc., Miami, Fla.

[21] Appl. No.: 312,720

[22] Filed: Feb. 21, 1989

Related U.S. Application Data

[63] Continuation-in-part of Ser. No. 43,525, Apr. 28, 1987, abandoned, which is a continuation-in-part of Ser. No. 792,587, Oct. 29, 1985, abandoned.

[51] Int. Cl.$^5$ .......................................... A31K 31/485
[52] U.S. Cl. ........................................................ 514/282
[58] Field of Search ........................................ 514/282

[56] References Cited

U.S. PATENT DOCUMENTS

| | | | |
|---|---|---|---|
| 3,896,226 | 7/1975 | Fishman | 514/282 |
| 4,416,886 | 11/1983 | Bernstein . | |
| 4,454,142 | 6/1984 | Tuttle | 514/282 |
| 4,639,455 | 1/1987 | Moore | 514/282 |
| 4,774,230 | 9/1988 | Tuttle et al. | 514/27 |
| 4,880,813 | 11/1989 | Frost | 514/282 |

FOREIGN PATENT DOCUMENTS

87/02586  5/1987  PCT Int'l Appl. .

OTHER PUBLICATIONS

Thornton et al., *Gut*, vol. 29, A726 (May 1988).
Merck Index, 10th Ed., Entry 2353 (1983).
Summerfield, *Br. J. Clin. Pharmac.*, 10:180–183 (1980).
Bernstein et al., *J. Am. Acad. Derm.*, 5:227–228 (1981).
Gal et al., *Anesthesiology*, 63:A508 (1985).
*Martindale The Extra Pharmacopoeia*, 28th ed., p. 2031 (1982).
Leslie et al., *Br. Med. J.*, 280:16–18 (1980).
Katovich et al., *Subst. Alc. Act./Misuse*, 5:87–95 (1984).
(Orbit Database Abstract of) Ho et al., *Gastroenterology*, 88:1665 (1985).
Dixon et al., *J. Pharm. Sci.*, 73:1645–1646 (1984).
Dixon et al., *Clin. Pharmacol. Ther.*, 39:49–53 (1986).
Thornton and Losowsky, *J. Hepatology*, 4:15 (1987).
Thornton and Losowsky, *Clin. Sci.*, 72(Supp. 16):30P (1987).
Thornton and Losowsky, *Clin. Sci.*, 72(Supp. 16):90P–91P (1987).
Thronton and Losowsky, *Brit. Soc. Gastroenterology, Abstract from Spring Meeting (3/23–3/25/88)*.
Thornton and Losowsky, *Br. Med. J.*, 297:1500–1504 (1988).

*Primary Examiner*—Donald G. Daus
*Attorney, Agent, or Firm*—Kirschstein, Ottinger, Israel & Schiffmiller

[57] ABSTRACT

A method of treating a mammal suffering from pruritus, whether antigen-induced or disease-induced, comprising orally administering to the subject from about 1 to about 25 mg of the narcotic antagonist nalmefene for an initial period of 1 to 7 days, and gradually increasing the dosage level of nalmefene by increments of 1 to 25 mg per day during successive periods of 1 to 7 days to a maximum of 150 mg per day. Clonidine or clonidine hydrochloride may be administered concomitantly with the nalmefene to alleviate opioid withdrawal symptoms.

4 Claims, No Drawings

METHOD OF TREATING PRURITUS WITH NALMEFENE AND CLONIDINE

CROSS-REFERENCE TO RELATED APPLICATION

This application is a continuation-in-part of application Serial No. 07/043,525, filed Apr. 28, 1987, now abandoned, which was a continuation-in-part of Ser. No. 792,587, filed Oct. 29, 1985, now abandoned.

BACKGROUND OF THE INVENTION

A large segment of the population suffers from antigen-induced allergies. Typical allergic responses include rhinitis, urticaria, eczema, skin flushing, pruritus, angioedema and bronchoconstriction (asthma). A large number of preparations are available to persons suffering from such allergic symptoms which are useful in alleviating the symptoms described above. Desirable qualities for relief of such symptoms include effectiveness of relief, length of effective action and safety of active ingredient. However, most anti-allergic preparations cause undesirable side effects in many patients taking the medication, e.g., drowsiness, dry mouth, etc.

It is known that certain opioids can precipitate asthma attacks in sensitive patients, and that morphine and related opioids are to be avoided during asthma attacks due to inherent respiratory depressant activity. It is also known that morphine may cause pruritus in certain individuals, which may be related to the degranulation of mast cells. Degranulation of mast cells is believed to play a central role in causing allergic responses.

Bernstein and Swift (*Arch. Dermatol.*, 155:1366, Nov. 1979) have shown that subcutaneous administration of the narcotic antagonist naloxone blocked pruritus caused by primary biliary cirrhosis. The same article showed that administering an enkephalin analog with opioid-like activity precipitated an asthma attack in one patient. Bernstein U.S. Pat. No. 4,181,726 discloses treatment of itching associated with Hodgkin's disease, mycosis fungoides, intractable pruritus and the like by injection of naloxone. Parenteral administration of naloxone for treating antigen-induced itch, asthma, urticaria and angioedema is similarly disclosed by Smitz et al., *Ann. Intern. Med.*, 97(5): 788–90 (1982).

It is well recognized in the field of opiate agonism and antagonism that there are multiple opiate receptor sub-species, each receptor having its own particular affinity for narcotics and antagonists thereof. The presence of multiple receptors for opiates and antagonists thereof creates a general unpredictability in the structure-activity relationship for narcotics and narcotic antagonists, as described in Goodman and Gilman's *The Pharmacological Basis of Therapeutics*, 6th ed., the teachings of which are incorporated herein by reference.

SUMMARY OF THE INVENTION

The present invention is directed to a method of treating pruritus, comprising the oral administration to a mammal in need of such treatment of an effective antipruritic amount of the narcotic antagonist nalmefene. The treatment of pruritus encompasses pruritus due to an antigen-induced allergic response, and also non-allergy related pruritus, such as organic disease-induced itching.

DETAILED DESCRIPTION OF THE INVENTION

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570) and sudden infant death syndrome (U.S. Pat. No. 4,639,455), among others.

The method of the present invention consists of the oral administration to a mammal suffering from allergic (i.e., antigen-induced) or non-allergic pruritus of from about 1 to about 150 mg of nalmefene on a daily basis. The term "non-allergic pruritus" as used herein includes pruritus caused by organic disease such as liver disease (e.g., cirrhosis), skin disease (e.g., eczema or psoriasis) and edema, such as angioedema.

In preparing oral pharmaceutical compositions containing nalmefene for use in the present invention, inert, pharmaceutically acceptable carriers are used which may be either solid or liquid. Solid form preparations include powders, tablets, dispersible granules, capsules and caplets. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably are comprised of from 5 to about 70 percent active ingredient on a weight/weight basis. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. Tablets, powders, caplets and capsules can be used as solid dosage forms suitable for oral administration.

Liquid form preparations include solutions, suspensions and emulsions. Liquid preparations can be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

In accordance with the present invention, animal (mammal) or human patients suffering from allergic or non-allergic pruritus are administered from about 1 to about 150 mg of nalmefene per day in one to four divided doses, preferably one to two doses. However, because some patients, particularly patients who may have elevated endogenous opioid levels (e.g., patients suffering from hepatic disease), may experience significant opioid withdrawal symptoms when nalmefene is first administered, it is preferred that the drug be introduced to the patient at low dosage levels (for example, 1 to 25 mg daily) with the dosage being raised in gradual increments (e.g., increments of 1 to 25 mg) over a period of time. As an example of such a dosage regimen, nalmefene may be orally administered to pruritus patients in doses of 1–5 mg b.i.d. or t.i.d. (i.e., two or three times daily) for an initial period of one to seven days, with the dosage then being increased by increments of 1–5 mg b.i.d or t.i.d. during successive periods of one to seven days up to a maximum of 75 mg b.i.d. or 50 mg t.i.d.

It has now been discovered that by administering nalmefene in a gradually increasing dosage regimen as described above, patients suffering from pruritus develop a substantial level of tolerance to the opioid-withdrawal side effects that may be induced by nalmefene (e.g., nausea, abdominal pain and raised arterial pressure), yet do not develop a corresponding tolerance to the pruritus-relieving effects of the drug. In fact, substantial relief of pruritus is maintained in most patients even while the withdrawal side effects disappear.

The unexpected finding that tolerance to the opioid withdrawal effects produced by nalmefene develops without a corresponding tolerance to the anti-pruritic effect enables successful treatment of pruritus patients with the drug on a long-term basis.

In patients who experience particularly severe withdrawal symptoms upon initial nalmefene administration, the antiadrenergic agent clonidine (or clonidine hydrochloride), sometimes used as an aid to heroin withdrawal, may be administered concomitantly with the nalmefene until the adverse side effects subside. From about 25–250 $\mu$g of clonidine may be administered to such patients one to four times daily during an initial period, for a total daily dosage of 25–1,000 $\mu$g. The dosage of clonidine is preferably gradually reduced as the side effects subside until the clonidine is eliminated entirely. The administration of clonidine as an adjunct to nalmefene has not been found to impact upon the anti-pruritic effectiveness of the latter drug.

The following example provides a detailed illustration of the method of the present invention and of the results achieved in a clinical trial. This example is not intended to limit or restrict the scope of the invention in any way, and should not be construed as providing dosage forms, regimens or methods of administration which must be utilized exclusively to practice the invention.

EXAMPLE

Eleven patients with liver disease (nine suffering from primary biliary cirrhosis, one from cryptogenic cirrhosis and one from alcoholic cirrhosis) were treated with oral nalmefene on an inpatient, unblinded basis. The nine patients with primary biliary cirrhosis all suffered from pruritus which had not responded well to prior drug treatments. To assess whether nalmefene was beneficial in alleviating these patients' itching, all other anti-pruritic agents were stopped three weeks before the study. Pruritus was measured daily for two weeks before the study and then at two weeks, one, three and six months after commencement of the study. Patients scored their pruritus levels on a visual analogue scale consisting of a 10 cm line ranging from "no itching" (0) to "very itchy" (10).

All eleven patients were given doses of nalmefene which were gradually increased over seven to ten days from 5 mg b.i.d. to 20–40 mg t.i.d. To minimize side effects, 100 $\mu$g of clonidine was given t.i.d. on the first three days of treatment and was reduced to 75 $\mu$g t.i.d. on day four, 50 $\mu$g t.i.d. on day five and 25 $\mu$g t.i.d. on day six. Clonidine was stopped entirely on day seven.

All nine patients with pruritus noticed an immediate, considerable improvement in this symptom. At one month after commencement of the study their pruritus scores had fallen from a median of 7.6 to a median of 0.2 ($p < 0.001$) and this improvement was sustained at three months (median 0.2) and six months (median 0.3).

Although all the patients experienced opioid withdrawal symptoms when first given nalmefene and clonidine, most of these symptoms subsided within two or three days, although four patients had intermittent abdominal pain for up to two months.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A method of treating a human patient suffering from pruritis comprising: (a) orally administering to said patient from about 1 to about 25 mg. of nalmefene per day for an initial period, (b) gradually increasing the amount of nalmefene administered in successive periods by about 1 to about 25 mg. per day up to a maximum of about 150 mg. per day, and (c) orally administering from about 25 to about 1,000 mg, of clonidine or clonidine hydrochloride to the patient daily concomitantly with the nalmefene, whereby tolerance develops to any opioid withdrawal symptoms induced by the nalmefene while the patient's pruritus is substantially alleviated".

2. A method according to claim 1 wherein said clonidine or clonidine hydrochloride is administered to the patient daily in 1 to 4 divided doses.

3. A method according to claim 2 wherein a first amount of clonidine or clonidine hydrochloride is administered daily to the patient during the initial period and the amount of clonidine or clonidine hydrochloride is gradually decreased during the successive periods as the patient's opioid withdrawal symptoms subside.

4. A method according to claim 3 wherein about 10 mg of nalmefene and 300 $\mu$g of clonidine are administered daily during the initial period, the dosage of nalmefene is increased during the successive periods to about 60–120 mg per day and the dosage of clonidine is reduced during the successive periods until it is eliminated entirely.

* * * * *